United States Patent [19]

Hirano et al.

[11] 4,447,522
[45] May 8, 1984

[54] METHOD OF FORMING A PHOTOGRAPHIC IMAGE

[75] Inventors: Shigeo Hirano; Yoshihiro Takagi, both of Kanagawa, Japan

[73] Assignee: Fuji Photo Film Co., Ltd., Kanagawa, Japan

[21] Appl. No.: 486,174

[22] Filed: Apr. 18, 1983

Related U.S. Application Data

[62] Division of Ser. No. 345,502, Feb. 3, 1982.

[30] Foreign Application Priority Data

Feb. 3, 1981 [JP] Japan ............................... 56-14565
Feb. 3, 1981 [JP] Japan ............................... 56-14566
Feb. 3, 1981 [JP] Japan ............................... 56-14567

[51] Int. Cl.³ ........................ G03C 5/24; G03C 1/02
[52] U.S. Cl. ................................. 430/405; 430/264; 430/566; 430/949; 430/448
[58] Field of Search ............... 430/423, 566, 405, 949, 430/264, 267, 963

[56] References Cited

U.S. PATENT DOCUMENTS

| | | | |
|---|---|---|---|
| 3,730,727 | 5/1973 | Olivares et al. | 430/566 |
| 4,230,796 | 10/1980 | Gunther et al. | 430/949 |
| 4,269,929 | 5/1981 | Nothnagle | 430/949 |
| 4,332,878 | 6/1982 | Akimura et al. | 430/264 |
| 4,385,108 | 5/1983 | Takagi et al. | 430/264 |

*Primary Examiner*—Mary F. Downey
*Attorney, Agent, or Firm*—Sughrue, Mion, Zinn, Macpeak & Seas

[57] ABSTRACT

A method of forming a photographic image which comprises development processing with an alkaline activator solution a silver halide photographic light-sensitive material comprising a support having thereon at least one surface latent image type silver halide emulsion layer, and containing in at least one layer selected from the silver halide emulsion layer and another hydrophilic colloid layer (1) a developing agents;
(2) an acylhydrazine compound represented by formula (I):

$$R^1NHNHCOR^2 \quad (I)$$

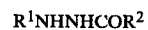

wherein $R^1$ represents an unsubstituted or substituted aryl group or alkyl group; and $R^2$ represents a hydrogen atom, or an unsubstituted or substituted aryl group or alkyl group; and (3) at least one compound represented by formula (II):

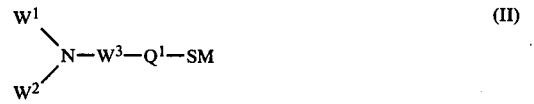

wherein each of $W^1$ and $W^2$ can represent a hydrogen atom or an aliphatic group or $W^1$ and $W^2$ are bonded each other to form a ring; $W^3$ represents a divalent aliphatic group; $Q^1$ represents a simple bond or a divalent heterocyclic group containing a nitrogen atom, an oxygen atom, or a sulfur atom; and M represents a hydrogen atom, an alkali metal atom, an alkaline earth metal atom, a quarternary ammonium salt, a quarternary phosphonium salt, or an amidino group, or an inorganic acid salt or an organic acid salt thereof.

According to the activator type developing method, a dot image having good dot quality and screen range can be obtained.

17 Claims, No Drawings

METHOD OF FORMING A PHOTOGRAPHIC IMAGE

This is a division of application Ser. No. 345,502, filed Feb. 3, 1982.

BACKGROUND OF THE INVENTION

The present invention relates to a method of forming a photographic image of very high contrast using a silver halide photographic light-sensitive material, and more particularly to a stable activator type developing method which can constantly provide an image having good quality in spite of variations in the stirring conditions of the processing solution.

In printing an original of continuous gradation by use of an offset printing plate or the like, the tone is reproduced by a collection of big and small points called "dots." These dots are very minute and are present in a number of 80 to 200 or more per square inch, and moreover they are required to be sharp individually. In the printing industry, therefore, a combination of a lith type light-sensitive material and a lith developer is employed, which enables formation of a dot image of high contrast by a specific development effect called a "lith effect."

The lith developer is an alkaline solution wherein the concentration of a sulfite acting as a preservative is generally controlled to extremely low levels and only hydroquinone is used as a developing agent. With a lith type light-sensitive material is developed with this solution, the tone of the lith type light-sensitive material is generally higher in contrast with a decrease in the concentration of sulfite ions.

However, since the general properties of the lith type light-sensitive material are greatly influenced by the concentration of the developing agent and are sensitive to changes in the concentration of bromine ions, it is difficult to steadily obtain an image of constant quality. Moreover, because of the very low concentration of sulfite ion as preservative in the lith developer, the lith developer after being prepared is very low in its resistance to oxygen in air and it is disadvantageously easily deteriorated.

Furthermore, in continuously processing the lith type light-sensitive material, the bromine ion is released from an emulsion layer and the developing agent is consumed as is the case with typical silver halide light-sensitive materials. Therefore, even if they are supplemented, it is necessary to check and correct the activity of the developer every several hours. This leads to troublesome or complicated daily production control.

In addition, in processing by such conventional methods, a long development time of from 1 minute to 2 minutes at a development temperature of from 25° C. to 35° C. has been needed to obtain sufficient blackening density and dot quality.

Therefore, methods have eagerly been desired which are able to provide dot images of super high contrast and of good dot quality and screen range.

Japanese Patent Application (OPI) No. 22438/76 (the term "OPI" as used herein refers to a "published unexamined Japanese patent application") discloses a method in which in order to avoid the use of the unstable lith developer, a hydroquinone based developing agent is introduced in a silver halide emulsion and the processing is carried out by use of an alkaline activator in the presence of a hydrazine compound such as hydrazine sulfate to obtain a negative image of high contrast.

This method improves the stability of the processing solution and accelerates the processing rate. This method, however, has the disadvantages that the dot quality obtained is inferior to those of conventional lith type light-sensitive materials, that dot characteristics suitable for use in the plate-making using a contact screen cannot be obtained, and that the screen range is of too high contrast, although contrast characteristics close to those of the lith type light-sensitive material can be obtained. Moreover, for light-sensitive materials in which hydrazine compounds containing an $NH_2NH-$ group have been introduced, it is difficult to hold the contrast characteristics obtained at the beginning of the production of the light-sensitive materials for a long period of time, which is commercially required. This seems due to the vigorous decomposition of the hydrazine compounds with time. Therefore, light-sensitive materials capable of providing images of high contrast cannot be obtained by such a method in which the hydrazine compounds of the type as described above are incorporated in the light-sensitive materials.

U.S. Pat. No. 2,419,975 discloses a method in which a hydrazine compound is added to a silver halide emulsion to obtain a negative image of high contrast. It is described therein that when the hydrazine compound is added to the silver chlorobromide emulsion and the development is carried out using a developer having a pH value as high as 12.8, photographic characteristics of very high contrast, with a $\gamma$ larger than 10, can be obtained. However, many of the hydrazine compounds as disclosed in this patent are of low stability in the light-sensitive materials and cannot be stored for extended periods of time. Also, for strongly alkaline developers having pH values close to 13, developing agents are easily oxidized by air and unstable, and they cannot be stored or used for extended periods of time. Moreover, the development time is nearly equal to those of conventional lith development. Furthermore, for use in the application of plate-making using a contact screen, such images having only the photographic characteristics of high contrast wherein $\gamma$ is 10 or more are inferior in dot quality, are of too high contrast in screen range, and therefore are not sufficiently satisfactory.

Hereinafter, the expressions "dot quality" and "screen range" as used herein will be explained in detail.

The expression "dot quality" means the quality of points when the blackening density is converted through a contact screen in the corresponding point area, and, in general, those having low fringe are preferred.

The expression "screen range" indicates the change of the dot area relative to the amount of exposure. Theoretically it is a characteristic to be determined depending on the density pattern of the contact screen used.

Therefore, even by the methods as described in the above cited references, if a contact screen having a density pattern suitable for a light-sensitive material to be used is chosen and used, a desirable screen range can be obtained. However, such choice of the suitable contact screen according to the type of the light-sensitive material used is undesirably very troublesome for those practically engaged in the operation of the plate-making.

Thus it has long been desired to produce light-sensitive materials which permit the formation of good dots, and which have low fringe, by use of a stable processing solution. Furthermore, it has been desired to produce, practically, the same screen range by use of the same contact screen as would be used in the conventional lith development without employing a special operation such as making of determination of an appropriate contact screen.

In order to overcome the above-described problems, the inventors have developed a method of rapidly obtaining a negative image of high contrast by processing a silver halide light-sensitive material containing an acylhydrazine compound which is stable in the silver halide light-sensitive material and a hydroquinone based developing agent with an alkaline activator solution, as described in Japanese Patent Application (OPI) Nos. 1936/81 and 9743/81. According to this method, an image of good dot quality and screen range is obtained, but it is desired to further improve dot quality. Furthermore, it has been found that according to such method there is a disadvantage in that the dot quality tends to be changed depending on the condition of stirring during processing.

SUMMARY OF THE INVENTION

Therefore, an object of the present invention is to provide a method of forming a negative image of very high contrast having a gamma ($\gamma$) value of more than 10 by use of a stable processing solution and a stable light-sensitive material.

Another object of the present invention is to provide a method of forming a dot image by use of a stable processing solution and a stable light-sensitive material which permits the dot image having a good dot quality to be formed more rapidly than in the case that a conventional lith developer is used.

Still another object of the present invention is to provide a method of forming a dot image having a dot quality superior to that obtained by the method described in Japanese Patent Application (OPI) Nos. 1936/81 and 9743/81.

A further object of the present invention is to provide a method of forming a dot image in which control of processing solution and operation of processing are simple, and in which the dot quality does not change depending on variations in the operation of processing are simple, and in which the dot quality does not change depending on variations in the operation of processing, particularly variations in the conditions of stirring.

Other objects of the present invention will become apparent from the following detailed description and examples.

These objects of the present invention can be attained by a method of forming a photographic image which comprises development processing with an alkaline activator solution a silver halide photographic light-sensitive material comprising a support having thereon at least one surface latent image type silver halide emulsion layer, and containing in at least one layer selected from the silver halide emulsion layer and another hydrophilic colloid layer.

(1) a developing agent;
(2) an acylhydrazine compound represented by formula (I):

(I)

wherein $R^1$ represents an unsubstituted or substituted aryl group or alkyl group; and $R^2$ represents a hydrogen atom or an unsubstituted or substituted aryl group or alkyl group; and (3) at least one compound selected from the group consisting of (3a) a compound represented by formula (II), (3b) a compound represented by formula (III), and (3c) a compound represented by formula (IV):

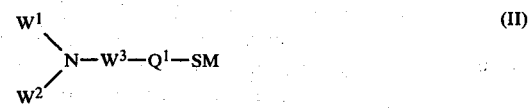

wherein each of $W^1$ and $W^2$ can represent a hydrogen atom or an aliphatic group or $W^1$ and $W^2$ are bonded each other to form a ring; $W^3$ represents a divalent aliphatic group; $Q^1$ represents a simple bond or a divalent heterocyclic group containing a nitrogen atom, an oxygen atom, or a sulfur atom; and M represents a hydrogen atom, an alkali metal atom, an alkaline earth metal atom, a quarternary ammonium salt, a quarternary phosphonium salt, or an amidino group, or an inorganic acid salt or an organic acid salt thereof;

wherein each of $W^4$, $W^5$, $W^6$, and $W^7$ can represent an aliphatic group or an aryl group and $W^4$ and $W^5$, $W^6$ and $W^7$ or $W^5$ and $W^7$ can be bonded to each other to form a ring; and

wherein $Q^2$ represents a sulfur atom or an oxygen atom; each of $W^8$ and $W^9$ can represent an aliphatic group, an aryl group, a heterocyclic group, or an amino group, and $W^8$ and $W^9$ can be bonded to each other to form a ring; and $W^{10}$ can represent an aliphatic group or an aryl group, and $W^9$ and $W^{10}$ can be bonded to each other to form a ring.

DETAILED DESCRIPTION OF THE INVENTION

The developing agent for use in the present invention is contained in at least one of the silver halide emulsion layer and other photographic constituting layers, particularly hydrophilic colloidal layers. Developing agents which can be used in the present invention include dihydroxybenzenes such as hydroquinone, chlorohydroquinone, bromohydroquinone, isopropylhydroquinone, methylhydroquinone, 2,3-dichlorohydroquinone, 2,5-dimethylhydroquinone, t-butylhydroquinone, hydroquinone monosulfonate, etc., 3-pyrazolidones such as 1-phenyl-3-pyrazolidone, etc., aminophenols such as N-methyl-p-aminophenol. They can be used alone or in combination with each other. Of these compounds, dihydroxybenzenes are preferred from a practical standpoint, and hydroquinones, and specifically hydroquinone are preferred because they provide a high gamma value.

The developing agent can be incorporated in the silver halide light-sensitive material by use of hitherto known methods. For example, the developing agent can be dissolved in an organic solvent compatible with water which is selected from alcohols, glycols, ketones, esters, amides and the like, and which exerts no adverse influences on the photographic characteristics. It is then added as a solution to at least one of the silver halide emulsion and a coating solution to form another layer and coated. The method described in Japanese Patent Application (OPI) No. 39928/1975 in which a developing agent is added as an oil dispersion to an emulsion can be employed. Moreover, the developing agent can be dissolved in a gelatin solution, added as a gelatin solution, and coated. Furthermore, there can be employed the method described in Japanese Patent Publication No. 15461/1970 in which the developing agent is dispersed in alkyl acrylates, alkyl methacrylates, or polymers such as cellulose esters, and the dispersion thus obtained is added and coated.

The amount of the developing agent contained in the silver halide light-sensitive material is from 0.1 to 5 mol per mol of silver halide, and preferably 0.1 to 2 mol per mol of silver halide.

Hereinafter the compounds represented by the general formula (I) will be explained in greater detail.

In the general formula (I), the aryl group which may be substituted represented by $R^1$ is a mono- or dicyclic aryl group, including benzene and naphthalene rings. Particularly preferred among them is the benzene ring.

The aryl group may be substituted, and examples of preferred substituents include a straight, branched or cyclic alkyl group preferably containing from 1 to 20 carbon atoms, for example, a methyl group, an ethyl group, an isopropyl group, an n-dodecyl group, etc., an aralkyl group, preferably a mono- or dicyclic aralkyl group having an alkyl moiety containing from 1 to 3 carbon atoms, for example, a benzyl group, etc., an alkoxy group preferably containing from 1 to 20 carbon atoms, for example, a methoxy group, an ethoxy group, etc., a substituted amino group, preferably substituted with an alkyl group containing from 1 to 20 carbon atoms, for example, a dimethylamino group, a diethylamino group, etc., an aliphatic acylamino group preferably having an alkyl group containing from 2 to 21 carbon atoms, for example, an acetylamino group, a heptylamino group, etc., an aromatic acylamino group preferably having a mono- or dicyclic aryl group, for example, a benzoylamino group, etc., or a group represented by the formula $X-(Y)_{\overline{n}}$.

In the group represented by the formula $X-(Y)_{\overline{n}}$, n represents 0 or 1; Y represents a divalent connecting group, for example, —CONH—, —$R^{11}$—CONH—, —O—$R^{11}$—CONH—, —S—$R^{11}$—CONH—, —$R^{11}$—, —$R^{11}$—O—$R^{12}$—, —$R^{11}$—S—$R^{12}$—, —$SO_2$NH—, —$R^{11}$—$SO_2$NH—, —NHCONH—, —$CH_2$—CH—N—, —$R^{11}$—NH—, —$R^{11}$—O—$R^{12}$—CONH—, —NHCO—$R^{11}$—, —NHCO—$R^{11}$—CONH—, —$R^{11}$—$R^{12}$—, etc., wherein $R^{11}$ and $R^{12}$ (which may be the same or different) each represents a divalent saturated or unsaturated aliphatic group, for example, an ethylene group, a butenylene group, a 1-methylpropylene group, a 1-methylmethylene group, etc., or a divalent aromatic group which may be substituted with a substituent such as an amino group, for example, a phenylene group, a naphthylene group, a 5-amino-1,2-phenylene group, etc. In —$R^{11}$—$R^{12}$—, $R^{11}$ and $R^{12}$ are different divalent groups.

X represents a group containing (1) a

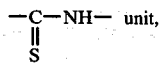

unit, (2) a group containing

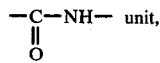

unit, (3) a group represented by

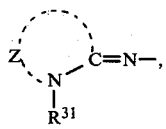

(4) a heterocyclic group, (5) an aralkyl group when n is 1, or (6) an aryl group substituted with an alkyl group.

The heterocyclic group represented by X is a 5-membered or 6-membered ring containing at least one hetero atom which may be condensed with an aromatic ring, particularly a benzene ring, and preferably a monovalent group derived from a heterocyclic compound (for example, a 1,2-benzotriazol-5-yl group, a 5-tetrazolyl group, an indazol-3-yl group, a 1,3-benzimidazol-5-yl group, a hydroxytetraazainden-2- or -3-yl group, etc.), a monovalent group derived from a heterocyclic quaternary ammonium salt (for example, an N-ethylbenzothiazolinium-2-yl group, an N-sulfoethylbenzothiazolinium-2-yl group, an N,N-dimethylbenzimidazolinium-2-yl group, etc.), a monovalent group derived from a heterocyclic compound having a mercapto group (for example, a 2-mercaptobenzothiazol-5- or -6-yl group, a 2-mercaptobenzoxazol-5- or -6-yl group, etc.).

The alkyl group represented by X is a mono- or dicyclic aralkyl group having an alkyl moiety containing 1 to 3 carbon atoms includes, for example, a benzyl group, etc.

The aryl group substituted with an alkyl group represented by X includes, for example, a 2,4-di-tert-amyl-1-phenyl group, etc.

The group containing a $$-\underset{\underset{S}{\|}}{C}-NH-\text{ unit}$$

represented by X preferably is an $$R^{21}-\underset{\underset{S}{\|}}{C}-NH-\text{ group,}$$

an $$R^{21}-S-\underset{\underset{S}{\|}}{C}-NH-\text{ group, an } R^{21}-\underset{\underset{R^{22}}{|}}{N}-\underset{\underset{S}{\|}}{C}-\underset{\underset{R^{23}}{|}}{N}-\text{ group,}$$

an $R^{21}-R^{11}-NH-\underset{\underset{S}{\|}}{C}-NH-$ group, etc.

The group containing

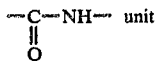 unit represented by X preferably is an

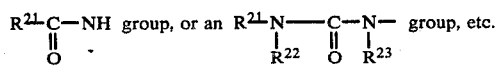

In the above formulae, $R^{21}$ can represent an aliphatic group (for example, an alkyl group, a cycloalkyl group, an alkenyl group, etc.), an aromatic group (for example, a phenyl group, a naphthyl group, etc.), or a heterocyclic group (for example, a thiazolyl group, a benzothiazolyl group, an imidazolyl group, a thiazolinyl group, a pyridinyl group, a tetrazolyl group, etc.); $R^{22}$ represents a hydrogen atom, an aliphatic group as defined for $R^{21}$ or an aromatic group as defined for $R^{21}$; $R^{23}$ can represent a hydrogen atom or an aliphatic group as defined for $R^{21}$; and $R^{11}$ has the same meaning as defined above, and at least one of $R^{22}$ and $R^{23}$ is a hydrogen atom. $R^{21}$ and $R^{23}$ can also be bonded together to form a ring. Preferred examples of the ring include the following:

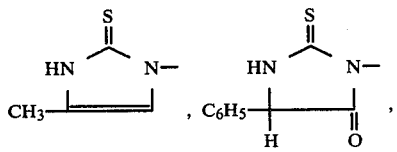

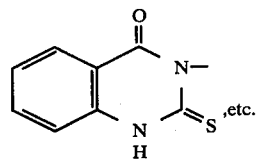

The group represented by $R^{21}$ or $R^{22}$ may be substituted with an alkoxy group, an alkoxycarbonyl group, an aryl group, an alkyl group, a dialkylamino group, an alkylthio group, a mercapto group, a hydroxy group, a halogen atom, a carboxy group, a nitro group, a cyano group, a sulfonyl group, a carbamoyl group, etc.

In the group represented by the formula

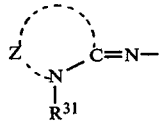

for X, Z represents a group of non-metallic atoms forming together with

a 5-membered or 6-membered heterocyclic ring. Specific examples of the heterocyclic ring include, for example, a thiazoline ring, a benzothiazoline ring, a naphthothiazoline ring, a thiazolidine ring, an oxazoline ring, a benzoxazoline ring, an oxazolidine ring, a selenazoline ring, a benzoselenazoline ring, an imidazoline ring, a benzimidazoline ring, a tetrazoline ring, a triazoline ring, a thiadiazoline ring, a 1,2-dihydropyridine ring, a 1,2-dihydroquinoline ring, a 1,2,3,4-tetrahydroquinoline ring, a perhydro-1,3-oxazine ring, a 2,4-benz[d]oxazine ring, a perhydro-1,3-thiazine ring, a 2,4-benz[d]thiazine ring, an uracil ring, etc.

$R^{31}$ represents a hydrogen atom or a saturated or unsaturated aliphatic group (for example, an alkyl group, an alkenyl group, an alkynyl group, etc.) which may be substituted with an alkoxy group, an alkylthio group, an acylamino group, an acyloxy group, a mercapto group, a sulfo group, a carboxy group, a hydroxy group, a halogen atom, an amino group, etc.

Of the above-described groups represented by X, particularly preferred groups are the group containing

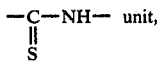

the group represented by

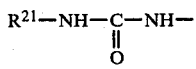

and the group represented by the formula

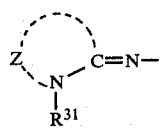

In formula (I), the alkyl group which may be substituted represented by $R^1$ is an alkyl group containing 1 to 10 carbon atoms and which is substituted with a substituent as defined for the aryl group described above.

For a group represented by $R^1$ in formula (I), the aryl group which may be substituted is more preferred than the alkyl group which may be substituted.

In formula (I), the aryl group which may be substituted represented by $R^2$ includes a mono- or dicyclic aryl group, for example, a group containing a benzene ring or a naphthalene ring and, particularly preferred, a benzene ring. The aryl group may be substituted with a substituent, for example, a halogen atom, a cyano group, a carboxy group, a sulfo group, etc. Preferred examples of the aryl group represented by $R^2$ include a phenyl group, a 4-chlorophenyl group, a 4-bromophenyl group, a 3-chlorophenyl group, a 4-cyanophenyl group, a 4-carboxyphenyl group, a 4-sulfophenyl group, a 3,5-dichlorophenyl group, a 2,5-dichlorophenyl group, etc.

In formula (I), the alkyl group which may be substituted represented by $R^2$ is preferably an alkyl group containing from 1 to 4 carbon atoms, which may be substituted with a substituent, for example, a halogen atom, a cyano group, a carboxy group, a sulfo group, etc. Examples of particularly preferred alkyl groups include a methyl group, an ethyl group, an n-propyl group, an isopropyl group, etc.

Of the compounds represented by the formula (I), those described in Japanese patent application (OPI) Nos. 10921/78, 20922/78 and 66732/78, Japanese patent application (OPI) Nos. 52050/80 and 90940/80, Japanese patent application (OPI) No. 20318/78, *Research*

Disclosure, 17626 (1978, No. 176), etc., are preferred. Particularly preferred compounds are those described in Japanese patent application (OPI) Nos. 10921/78, 20922/78 and 66732/78.
Specific examples of the compounds represented by formula (I) are shown below, but the present invention is not limited thereto.
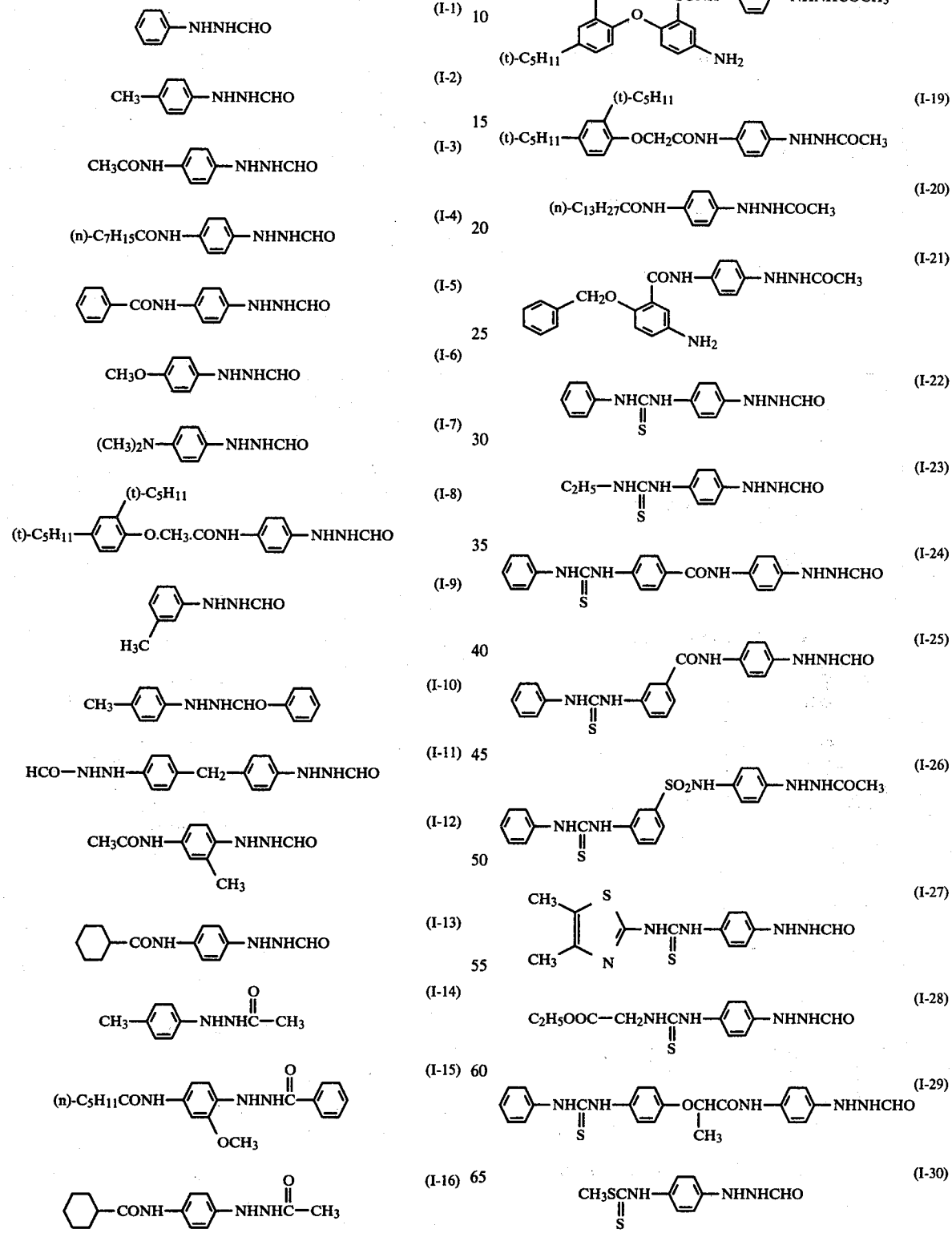

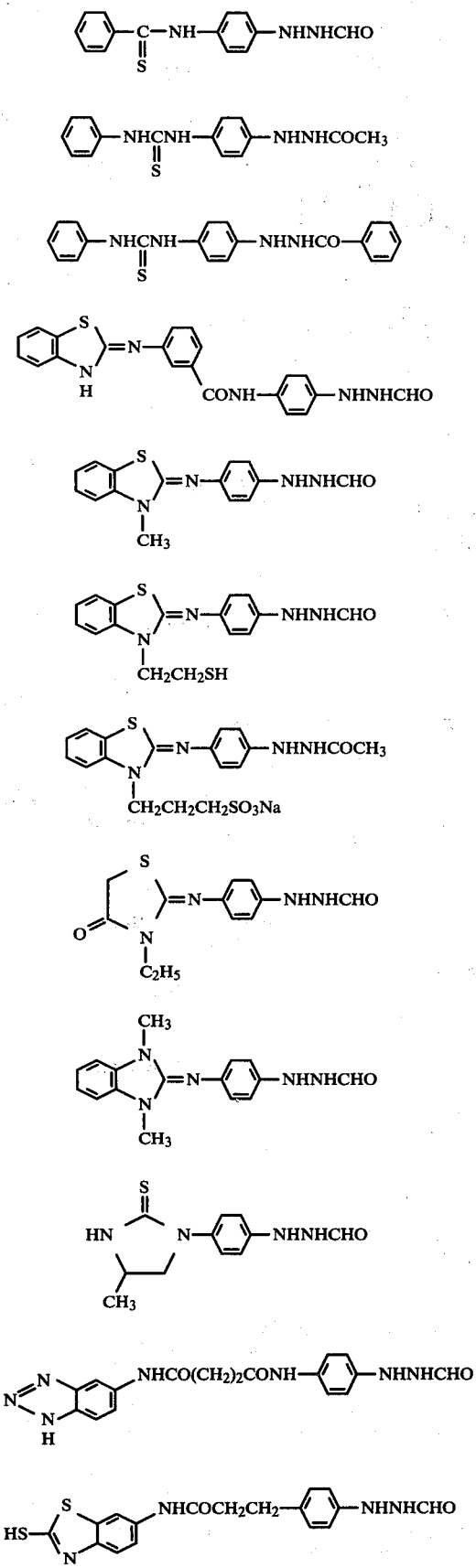

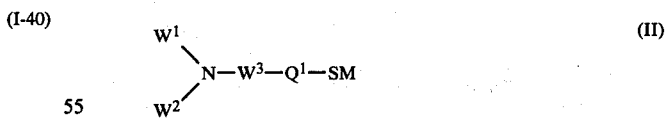

Synthesis methods for these compounds are described in Japanese patent application (OPI) Nos. 10921/78, 20922/78 and 66732/78, Japanese patent application (OPI) Nos. 52050/80 and 90940/80, etc.

The compound represented by formula (I) described above is added to at least one layer of a silver halide photographic light-sensitive material in a preferred range of from $10^{-8}$ mol/mol Ag to $10^{-1}$ mol/mol Ag, and particularly preferably from $10^{-6}$ mol/mol Ag to $10^{-2}$ mol/mol Ag.

By further incorporating at least one compound selected from the group consisting of a compound represented by formula (II) described below, a compound represented by formula (III) described below and a compound represented by formula (IV) described below into at least one photographic constituting layer of a silver halide light-sensitive material of substantially the surface latent image type which containing the above described developing agent and acylhydrazine compound and processing the light-sensitive material with an alkaline activator solution, an image of better dot quality can be obtained, and, at the same time the variation of dot quality due to changes in the condition of stirring during processing can be prevented.

$$\begin{matrix} W^1 \\ \phantom{W}\diagdown \\ \phantom{WWW}N-W^3-Q^1-SM \\ \phantom{W}\diagup \\ W^2 \end{matrix} \qquad (II)$$

In formula (II), $W^1$ and $W^2$, which may be the same or different, each represents a hydrogen atom or an aliphatic group or $W^1$ and $W^2$ are bonded each other to form a ring; $W^3$ represents a divalent aliphatic group; $Q^1$ represents a simple bond or a divalent heterocyclic group containing a nitrogen atom, an oxygen atom or a sulfur atom; and M represents a hydrogen atom, an alkali metal atom, an alkaline earth metal atom, a quarternary ammonium salt, a quaternary phosphonium salt or an amidino group, or an inorganic acid salt or an organic acid salt thereof;

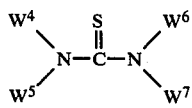
(III)

In formula (III), each of $W^5$, $W^6$ and $W^4$, to $W^7$ (which may be the same or different) can represent an aliphatic group or an aryl group, and $W^4$ and $W^5$, $W^6$ and $W^7$ or $W^5$ and $W^7$ can be bonded to each other to form a ring. Formula (IV) is represented by

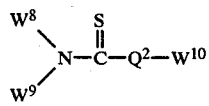
(IV)

In formula (IV), $Q^2$ represents a sulfur atom or an oxygen atom, each of $W^8$ and $W^9$ (which may be the same or different) can represent an aliphatic group, an aryl group, a hererocyclic group, or an amino group, and $W^8$ and $W^9$ are bonded each other to form a ring; and $W^{10}$ can represent an aliphatic group or an aryl group, and $W^9$ and $W^{10}$ can be bonded to each other to form a ring.

Hereinafter the compounds represented by formulae (II), (III) and (IV) will be explained in greater detail.

In formula (II), the aliphatic group represented by $W^1$ or $W^2$ is preferably an alkyl group, an alkenyl group or an alkynyl group, each of these groups containing from 1 to 12 carbon atoms and which may be substituted with an appropriate group, Examples of the alkyl group include, for example, a methyl group, an ethyl group, a propyl group, a butyl group, a hexyl group, a decyl group, a dodecyl group, an isopropyl group, a sec-butyl group, a cyclohexyl group, etc. Examples of the alkenyl group include, for example, an allyl group, a 2-butenyl group, a 2-hexenyl group, a 2-otenyl group, etc. Examples of the alkynyl group include, for example, a propargyl group, a 2-pentynyl group, etc. Examples of the substituents include, for example, a phenyl group, a substituted phenyl group, an alkoxy group, an alkylthio group, a hydroxy group, a carboxy group, a sulfo group, an alkylamino group, an amido group, etc.

The ring formed by $W^1$ and $W^2$ is a 5-membered or 6-membered carbocyclic ring or heterocyclic ring comprising a carbon atom, a nitrogen atom, and an oxygen atom, and preferably a saturated ring. Examples of such rings include

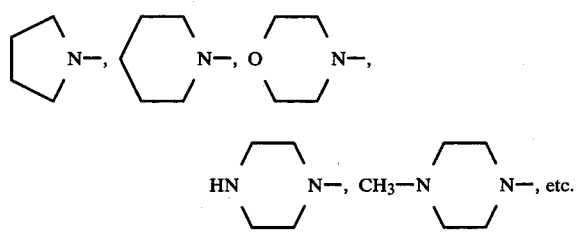

For $W^1$ or $W^2$, an alkyl group having from 1 to 3 carbon atoms is particularly preferred and an ethyl group is more preferred.

The divalent aliphatic group represented by $W^3$ is preferably $-Q^3-$ or $-Q^3S-$ wherein $Q^3$ represents a divalent aliphatic group, preferably having from 1 to 6 carbon atoms and which may be saturated or unsaturated. Examples of the divalent aliphatic groups include, for example, $-CH_2-$, $-CH_2CH_2-$, $-(CH_2)_3-$, $-(CH_2)_4-$, $-(CH_2)_6-$, $-CH_2CH=CHCH_2-$, $-CH_2C\equiv CCH_2-$, $-CH_2\underset{\underset{CH_3}{|}}{C}HCH_2-$, etc.

The preferred number of the carbon atoms for $Q^3$ is from 2 to 4. Particularly preferred groups for $Q^3$ are $-CH_2CH_2-$ and $-CH_2CH_2CH_2-$. When $Q^1$ represents a simple bond, $W^3$ represents only $-Q^3-$.

The divalent heterocyclic group represented by $Q^1$ is a 5-membered or 6-membered heterocyclic group containing at least one hetero atom selected from a nitrogen atom, an oxygen atom, or a sulfur atom, which may be condensed with a benzene ring. A preferred heterocyclic ring is an aromatic heterocyclic ring, for example, a tetrazole ring, a triazole ring, a thiadiazole ring, an oxadiazole ring, an imidazole ring, a thiazole ring, an oxazole ring, a benzimidazole ring, a benzothiazole ring, an benzoxazole ring, etc. Of these rings, a tetrazole ring and a thiadiazole ring are particularly preferred.

The alkali metal atom represented by M include, for example, $Na^+$, $K^+$, $Li^+$, etc.

The alkaline earth metal atom represented by M include, for example, $Ca^{++}$, $Mg^{++}$, etc.

The quarternary ammonium salt represented by M is a quarternary ammonium salt containing 4 to 30 carbon atoms and includes, for example, $(CH_3)_4N^\oplus$, $(C_2H_5)_4N^\oplus$, $(C_4H_9)_4N^\oplus$, $C_6H_5CH_2N^\oplus(CH_3)_3$, $C_{16}H_{33}N^\oplus(CH_3)_3$, etc.

The quarternary phosphonium salt represented by M includes, for example, $(C_4H_9)_4P^\oplus$, $C_{16}H_{33}P^\oplus(CH_3)_3$, $C_6H_5CH_2P^\oplus(CH_3)$, etc.

The inorganic acid salt of the compound represented of formula (II) includes, for example, a hydrochloric acid salt, a sulfuric acid salt, a nitric acid salt, a phosphoric acid salt, etc.

The organic acid salt of the compound represented by formula (II) includes, for example, an acetic acid salt, a propionic acid salt, a methanesulfonic acid salt, a benzenesulfonic acid salt, a p-toluenesulfonic acid salt, etc.

Specific examples of the compounds represented by formula (II) are shown below, but the present invention is not limited thereto.

(II-1)

(II-2)

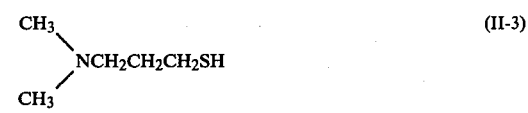
(II-3)

(II-4)

-continued

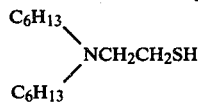 (II-5)

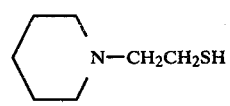 (II-6)

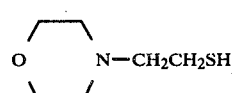 (II-7)

 (HOCH$_2$CH$_2$)$_2$NCH$_2$CH$_2$SH (II-8)

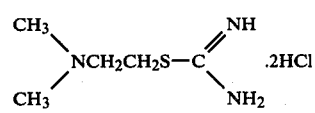 (II-9)

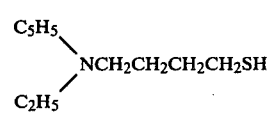 (II-10)

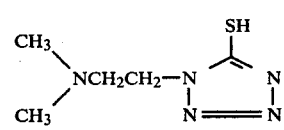 (II-11)

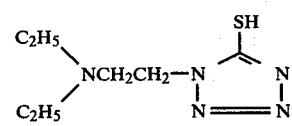 (II-12)

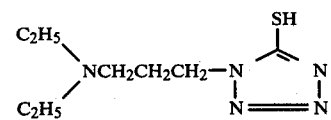 (II-13)

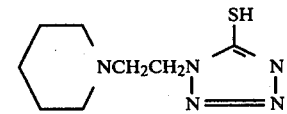 (II-14)

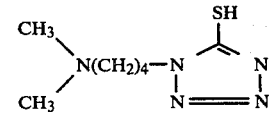 (II-15)

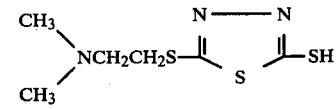 (II-16)

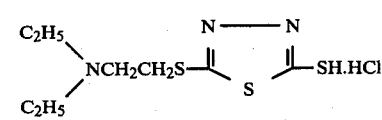 (II-17)

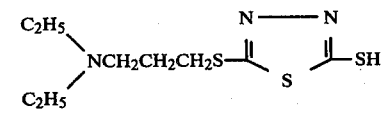 (II-18)

-continued

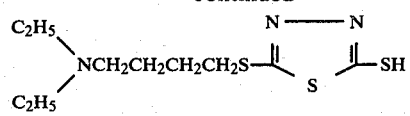 (II-19)

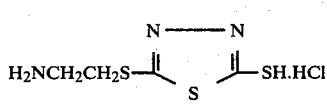 (II-20)

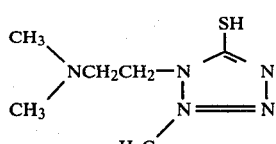 (II-21)

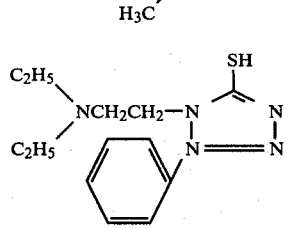 (II-22)

The compounds represented by the general formula (II) and inorganic acid salts or organic acid salts thereof can be obtained in the following manner. When $Q^1$ represents a simple bond, a mercapto group can be introduced by the reaction of a compound of the formula

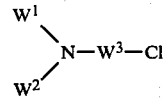

with thiourea. When $Q^1$ represents a heterocyclic group and $W^3$ represents —$Q^3$S—, the desired compounds can be synthesized by the reaction of a compound of the formula

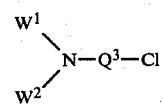

heterocyclic ring. When $Q^1$ represents a heterocyclic group and $W^3$ represents —$Q^3$—, the desired compound can be synthesized by introducing the heterocyclic ring using a ring-closing reaction as described for example, in Japanese patent application (OPI) Nos. 1475/1976, 50169/1978, etc.

Synthesis examples of the compounds represented by formula (II) and inorganic acid salts or organic salts thereof are shown below.

Synthesis of Compound (II-9)

43.2 g of dimethylaminoethyl chloride hydrochloric acid salt and 22.8 g of thiourea were reacted under refluxing by heating in a mixture of 86 ml of 1-butanol and 9 ml of water for 3 hours. After being allowed to stand for cooling, 165 ml of methanol was added to the reaction mixture and was cooled using ice. The crystals thus deposited were collected by filtration under reduced pressure and washed with acetone to obtain 55.7 g (Yield 84%) of the desired compound. Melting point of the compound was 178° to 179° C.

Synthesis of Compound (II-17)

15 g of 2,5-dimercapto-1,3,4-thiadiazole and 17.2 g of diethylaminoethyl chloride hydrochloric acid salt was dispersed in 75 ml of 1-butanol and to the mixture 7.9 g of pyridine was added while stirring at 80° C. After refluxing by heating for 2 hours, the reaction mixture was cooled with ice. The crystals thus deposited were collected by filtration and recrystallized from a mixture of ethanol and water (19:1) to obtain 22.6 g (Yield 79%) of the desired compound. Melting point of the compound was 184° to 186° C.

In formula (III), the aliphatic group represented by $W^4$, $W^5$, $W^6$, or $W^7$ is preferably an alkyl group (which may be substituted) or an alkenyl group (for example, an allyl group, etc.). The aryl group represented by $W^4$, $W^5$, $W^6$, or $W^7$ is preferably a phenyl group (which may be substituted). The total number of the carbon atoms included in $W^4$, $W^5$, $W^6$, and $W^7$ is preferably 30 or less. The ring formed from $W^4$ and $W^5$, $W^6$ and $W^7$, or $W^5$ and $W^7$ is a 5-membered or 6-membered heterocyclic ring, and includes, for example, an imidazolidinethione ring, a piperidine ring, a morpholine ring, etc. The alkyl group described above may be straight chain or branched chain. Examples of the substituents for the alkyl group include, for example, a hydroxy group, a carboxy group, a sulfo group, an amino group, an alkoxy group having an alkyl moiety containing from 1 to 5 carbon atoms, a phenyl group, a 5-membered or 6-membered heterocyclic group (for example, a furyl group, etc.), etc. Examples of the substituents for the aryl group include, for example, a hydroxy group, a carboxy group, a sulfo group, etc.

Of these compounds in which at least three of $W^4$, $W^5$, $W^6$, and $W^7$ are alkyl groups, each alkyl group has from 1 to 5 carbon atoms, and the total number of the carbon atoms included in $W^4$, $W^5$, $W^6$, and $W^7$ is 20 or less are particularly preferred.

Specific examples of the compounds represented by formula (III) are shown below, but the present invention is not limited thereto.

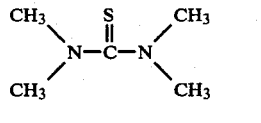
(III-1)

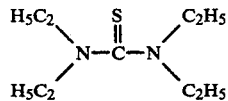
(III-2)

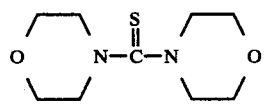
(III-3)

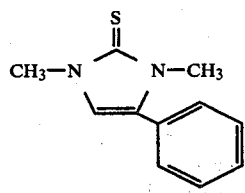
(III-4)

-continued

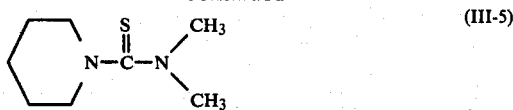
(III-5)

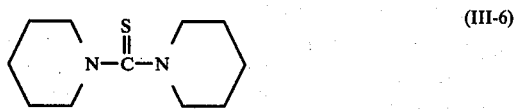
(III-6)

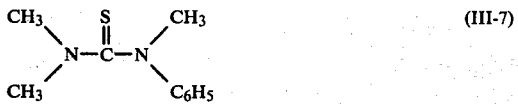
(III-7)

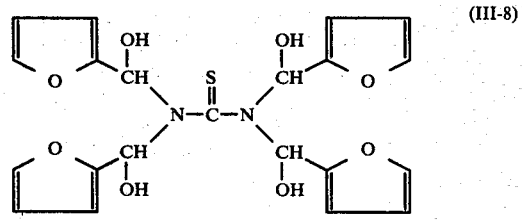
(III-8)

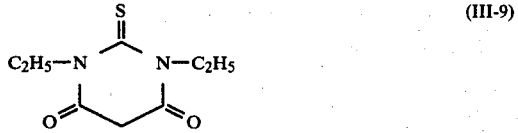
(III-9)

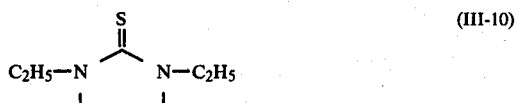
(III-10)

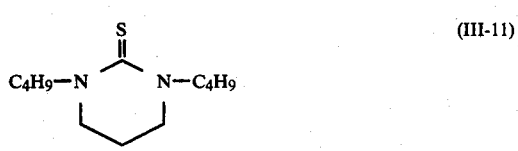
(III-11)

Methods for preparation of these compounds are described, for example, in J. Braun and K. Weizbach, *Berichte der Deutschen chemischen Gesellschaft*, Vol. 63, page 2846 (1930), V. Mozolis and S. Jokubaityte, *Lietuvos T S R Mokslu Akadeurijos Darbai. Ser. B*, Vol. 1969, No. 3, pages 125 to 131, H. Weidinger and H. Eilingsfeld, West German Pat. No. 1,119,843, R. A. Donia, *Journal of Organic Chemistry*, Vol. 14, pages 946 to 951 (1949), F. B. Zienty, *Journal of American Chemical Society*, Vol. 68, pages 1388 to 1389 (1946), L. G. S. Brooker, *Journal of American Chemical Society*, Vol. 73, pages 5329 to 5332 (1951), etc.

In formula (IV), $Q^2$ represents a sulfur atom or an oxygen atom. The aliphatic group represented by $W^8$ and $W^9$ is, preferably, for example, an unsubstituted or substituted alkyl group having from 1 to 4 carbon atoms in the alkyl moiety. The substituents for the alkyl group include, for example, a carboxy group, a sulfo group, a hydroxy group, an aryl group (preferably, a phenyl group, etc.), etc. Specific examples of the alkyl groups include, for example, a methyl group, an ethyl group, a propyl group, a butyl group, a carboxymethyl group, a carboxyethyl group, a carboxypropyl group, a sulfoethyl group, a sulfopropyl group, a sulfobutyl group, a hydroxyethyl group, a benzyl group, a phenethyl group, etc. The aryl group represented by $W^8$ or $W^9$ is, preferably, for example, an unsubstituted or substituted aryl group (preferably, a phenyl group, etc.). The substituents for the aryl group include, for example, an alkyl group (preferably, an alkyl group containing from 1 to 4 carbon atoms, etc.), a sulfo group, an alkoxy group (preferably, an alkoxy group containing from 1 to 4 carbon atoms in the alkyl moiety), a halogen atom, etc. Specific examples of the aryl groups include, for example, a phenyl group, a 2-methylphenyl group, a 4-sulfophenyl group, a 4-ethoxyphenyl group, a 4-chlorophenyl group, etc. The heterocyclic group represented by $W^8$ or $W^9$ is, preferably, for example, a 5-membered or 6-membered nitrogen containing heterocyclic group, and more specifically, for example, a 2-pyridyl group, a 3-pyridyl group, a 4-pyridyl group, etc. As the amino group represented by $W^8$ and $W^9$, a substituted amino group is particularly preferred, and includes, for example, an arylamino group (in which the aryl group is preferably an unsubstituted phenyl group or a substituted phenyl group substituted with a substituent, for example, an alkyl group, a sulfo group, a carboxy group, etc.). Specific preferred examples of the amino group includes, for example, a 4-sulfophenylamino group, etc.

The ring formed by bonding $W^8$ and $W^9$ is preferably a 5-membered or 6-membered heterocyclic ring (for example, a piperidine ring, a morpholine ring, a piperazine ring, etc.), etc.

The aliphatic group represented by $W^{10}$ is preferably, for example, an unsubstituted or substituted alkyl group containing 1 to 4 carbon atoms in the alkyl moiety. The substituents for the alkyl group include, for example, a carboxy group, a sulfo group, a hydroxy group, an aryl group (for example, a phenyl group, etc.), etc. Specific examples of the alkyl groups include, for example, a methyl group, an ethyl group, a propyl group, a butyl group, a carboxymethyl group, a carboxyethyl group, a carboxypropyl group, a sulfoethyl group, a sulfopropyl group, a sulfobutyl group, a hydroxyethyl group, a benzyl group, a phenethyl group, etc. The aryl group represented by $W^{10}$ is, preferably, for example, an unsubstituted or substituted aryl group (preferably, a phenyl group). The substituents for the aryl groups include, for example, an alkyl group (preferably, an alkyl group containing 1 to 4 carbon atoms), a sulfo group, an alkoxy group (preferably, an alkoxy group containing from 1 to 4 carbon atoms in the alkyl moiety), a halogen atom, etc. Specific examples of the aryl groups include, for example, a phenyl group, a 2-methylphenyl group, a 4-sulfophenyl group, a 4-ethoxyphenyl group, a 4-chlorophenyl group, etc.

The ring formed by bonding $W^9$ and $W^{10}$ is preferably a 5-membered or 6-membered heterocyclic ring. Of these, a compound represented by formula (IV′) described below, in which $W^9$ and $W^{10}$ are bonded each other to form a ring, is more preferred.

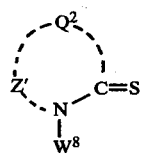

(IV′)

In formula (IV′), Z′ represents a group of atoms necessary to form a heterocyclic ring (including a heterocyclic ring having at least one ring selected from an unsaturated ring containing 5 to 6 carbon atoms, for example, a benzene ring, a tetrahydrobenzene ring, etc., fused thereto; and $Q^2$ and $W^8$ each has the same meaning as defined in formula (IV) above.

Now, the compounds represented by formula (IV′) will be explained in greater detail.

In formula (IV′), Z′ represents a group of atoms necessary to form a heterocyclic ring (as a heterocyclic ring itself, preferably a 5-membered ring), for example, a thiazolidine-2-thione ring (for example, a thiazolidine-2-thione ring, a 5-methylthiazolidine-2-thione ring, a 4-carboxythiazolidine-2-thione ring, etc.), a 4-thiazoline-2-thione ring (for example, a 4-methyl-4-thiazoline-2-thione ring, a 4-carboxymethyl-4-thiazoline-2-thione ring, a 4-carboxy-4-thiazoline-2-thione ring, etc.), a 1,3,4-thiadiazoline-2-thione ring (for example, a 5-ethylthio-1,3,4-thiadiazoline-2-thione ring, etc.), a benzothiazoline-2-thione ring (for example, a benzothiazoline-2-thione ring, a 5-carboxybenzothiazoline-2-thione ring, a 5-sulfobenzothiazoline-2-thione ring, a 5-methylbenzothiazoline-2-thione ring, etc.), a benzoxazoline-2-thione ring (for example, a benzoxazoline-2-thione ring, a 5-sulfobenzoxazoline-2-thione ring, a 5-methylbenzoxazoline-2-thione ring, etc.) or the like.

$W^8$ has the same meaning as defined for $W^8$ in formula (IV).

A cation which is a salt of a sulfo group or a carboxy group each of which is a nuclear substituent on the heterocyclic ring for $W^8$ or Z′ is preferably a cation which forms a water-soluble salt. Specifically, an alkali metal atom is preferred, and particularly, $Na^+$ and $K^+$ are preferred.

The nitrogen containing heterocyclic compounds represented by formula (IV′) include compounds represented by formulae (IVa) to (IVc) described below. In particular, the compounds represented by the general formula (IVa) are preferred.

(IVa)

(IVb)

(IVc)

In formulae (IVa), (IVb) and (IVc), $Q^2$ represents a sulfur atom or an oxygen atom, and a sulfur atom is preferred. A and B (which may be the same or different) each represents a hydrogen atom, a carboxy group, an aliphatic group, an aryl group or an alkoxycarbonyl group, or A and B can be bonded to each other and represent a group of atoms necessary to form an unsaturated ring containing 5 to 6 carbon atoms (this ring is preferably substituted with a substituent, for example, a sulfo group, a carboxy group, etc.). When A and B are bonded each other to form an unsaturated ring containing 5 to 6 carbon atoms, the compound represented by formula (IVa) contains at least one group selected from the member consisting of a hydroxy group, a sulfo group and a carboxy group in the molecule thereof. D represents a hydrogen atom, a carboxy group, an aliphatic group or an aryl group. $W^8$ has the same meaning as defined for $W^8$ in formula (IV). Each of E and G (which may be the same or different) represents a hydrogen atom, an aliphatic group or a carboxy group.

Now, the compounds represented by formulae (IVa) to (IVc) will be explained in greater detail.

In formulae (IVa) to (IVc), A and B each represents a hydrogen atom; a sulfo group; a carboxy group; an aliphatic group [for example, an unsubstituted or substituted alkyl group containing from 1 to 6 carbon atoms, preferably from 1 to 4 carbon atoms in the alkyl moiety. The substituents for the alkyl group include, for example, a hydroxy group, a halogen atom, a carboxy group, a sulfo group, an aryl group (preferably a phenyl group, etc.), etc. Specific examples of the alkyl groups include, for example, a methyl group, an ethyl group, a butyl group, a hydroxyethyl group, a sulfopropyl group, a carboxymethyl group, a benzyl group, etc.]; an aryl group [for example, an unsubstituted or substituted aryl group. The substituents for the aryl groups include, for example, an alkyl group, a hydroxy group, a halogen atom, a carboxy group, a sulfo group, etc. Specific examples of the aryl groups include, for example, a phenyl group, a 4-methylphenyl group, a 4-hydroxyphenyl group, a 3- or 4-chlorophenyl group, a 4-carboxyphenyl group, a 4-sulfophenyl group, etc.]; an alkoxycarbonyl group, preferably an alkoxycarbonyl group containing from 1 to 5 carbon atoms in the alkyl moiety, for example, an ethoxycarbonyl group, etc.; or A and B can be bonded to each other and represent a group of atoms necessary to form a ring containing one double bond and 5 to 6 carbon atoms (this ring is preferably substituted with a substituent, for example, a sulfo group, a carboxy group, etc., for example, a trimethylene group, a tetramethylene group, etc., or A and B are bonded to each other and represent a group of atoms necessary to form an unsubstituted or substituted benzene ring. The substituents for the benzene ring include, for example, an alkyl group (preferably an alkyl group containing from 1 to 4 carbon atoms, for example, a methyl group, an ethyl group, etc.), an aryl group (for example, a phenyl group, etc.), an alkoxy group (preferably, an alkoxy group containing from 1 to 4 carbon atoms in the alkyl moiety, for example, a methoxy group, an ethoxy group, etc.), a halogen atom (for example, a chlorine atom, a bromine atom, etc.), an alkyl group substituted with a carboxy group (preferably containing from 1 to 3 carbon atoms in the alkyl moiety, for example, a carboxymethyl group, etc.), an arylamino group (in which the aryl group is preferably a phenyl group, for example, an anilino group, etc.), a carboxy group, a sulfo group, or the like. D represents a hydrogen atom, a carboxy group, an aliphatic group, for example, an unsubstituted or substituted alkyl group containing from 1 to 6 carbon atoms, and preferably from 1 to 4 carbon atoms in the alkyl moiety. The substituents for the alkyl group include, for example, a hydroxy group, a sulfo group, a carboxy group, etc. Specific examples of the alkyl group include, for example, a methyl group, an ethyl group, a carboxymethyl group, a carboxyethyl group, a hydroxyethyl group, etc.] or an aryl group [for example, an unsubstituted or substituted aryl group (preferably a phenyl group). The substituents for the aryl group include, for example, a sulfo group, a carboxy group, etc. Specific examples of the aryl group include, for example, a phenyl group, a p-sulfophenyl group, etc.]. E and G each represents a hydrogen atom, an aliphatic group [for example, an unsubstituted or substituted alkyl group, and preferably containing from 1 to 4 carbon atoms. The substituents for the alkyl group include, for example, a carboxy group, etc. Specific examples of the alkyl groups include, for example, a methyl group, a carboxymethyl group, a carboxyheptyl group, etc.] or a carboxy group.

Specific examples of the compounds represented by formula (IV) are shown below, but the present invention is not limited thereto.

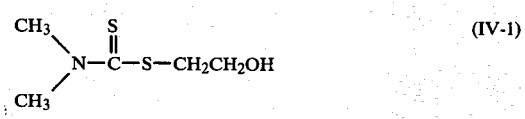 (IV-1)

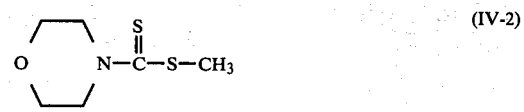 (IV-2)

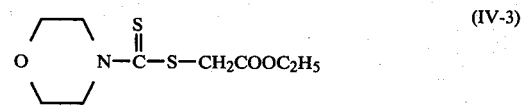 (IV-3)

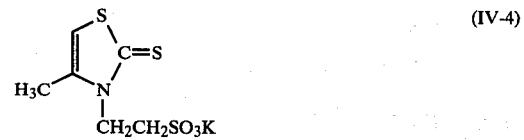 (IV-4)

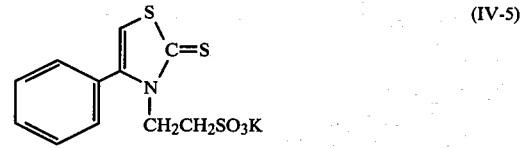 (IV-5)

 (IV-6)

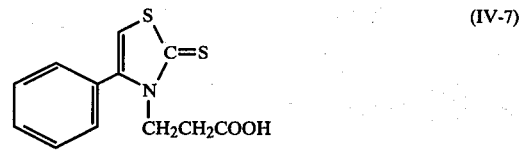 (IV-7)

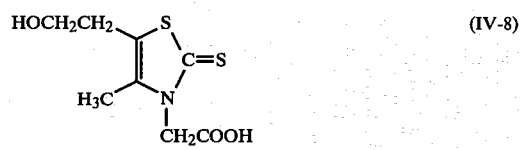 (IV-8)

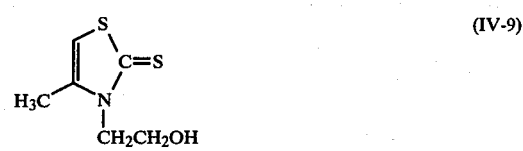 (IV-9)

-continued

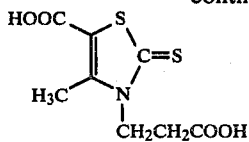
(IV-10)

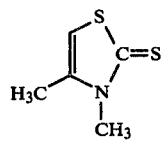
(IV-11)

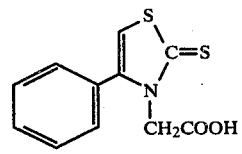
(IV-12)

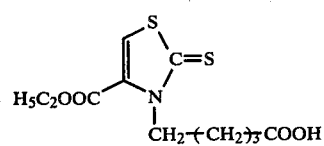
(IV-13)

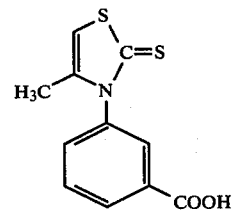
(IV-14)

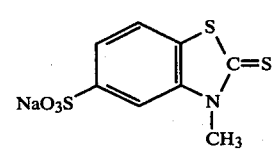
(IV-15)

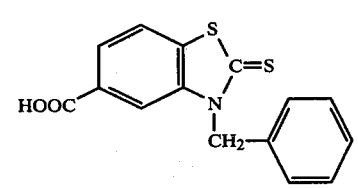
(IV-16)

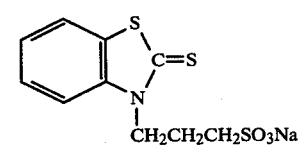
(IV-17)

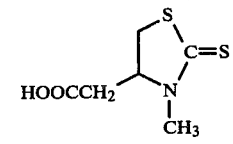
(IV-18)

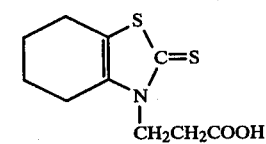
(IV-19)

Synthesis examples of the compounds represented by formula (IV) are shown below.

Synthesis of Compound (IV-2)

21.8 g (0.25 mol) of morpholine and 14 g (0.25 mol) of potassium hydroxide were dissolved in 200 ml of alcohol and to the solution, 19 g (0.25 mol) of carbon disulfide was added under cooling (at 5° C. or below) with stirring. After stirring for 2 hours, 35.5 g (0.25 mol) of methyl iodide was added and the mixture was refluxed by heating for 30 minutes. After cooling, the crystals thus deposited were collected by filtration and recrystallized from ethanol to obtain 22 g (yield 50%) of the desired compound. Melting point of the compound was 86° to 87° C.

Synthesis of Compound (IV-4)

To 200 ml of an aqueous solution containing 22.4 g (0.4 mol) of potassium hydroxide, 25 g (0.2 mol) of taurine was dissolved and to the solution, 100 ml of ethanol containing 15.2 g (0.2 mol) of carbon disulfide was added under cooling (at 5° C. or below) with stirring. The mixture was stirred for 2 hours at room temperature to complete the reaction. Then 18.5 g (0.2 mol) of monochloroacetone was added dropwise under cooling (at 5° C. or below) with stirring over about 30 minutes. After reacting at room temperature for 3 hours, the mixture was concentrated and the crystals thus-deposited were collected by filtration and dried. The crystals were suspended in ethanol and refluxed by heating for 30 minutes under acidic condition with sulfuric acid (at pH of about 3 to 4). After cooling the crystals thus-deposited were collected by filtration and recrystallized from a diluted aqueous potassium hydroxide solution to obtain 10 g (yield 20%) of the desired compound. Melting point of the compound was above 300° C.

Synthesis of Compound (IV-7)

To 250 ml of a methanol solution containing 44 g (0.5 mol) of β-aminopropionic acid and 28 g (0.5 mol) of potassium hydroxide, was added 30 ml (0.5 mol) of carbon disulfide under cooling (at 5° C. or below) and the mixture was stirred for 2 hours. A methanol solution containing 100 g (0.5 mol) of phenacyl bromide was added dropwise under cooling at 5° C. or below and after the completion of the addition the mixture was stirred at room temperature for 2.5 hours. 220 ml of water was added and the alcohol was distilled off under reduced pressure. The residue was acidified with hydrochloric acid (at pH of about 3 or 4) under cooling with ice with stirring and the crystals thus-deposited were collected and washed with water to obtain 116 g of 4-phenyl-3-(2-carboxyethyl)-4-hydroxythiazolidine-2-thione. Melting point of the compound was 132° C. The crystals were dissolved in 500 ml of glacial acetic acid and refluxed by heating for 30 minutes. After cooling, 1 liter of water was added to the mixture and the crystals thus-deposited were collected by filtration to obtain 89 g (yield 65%) of the desired compound. Melting point of the compound was 134° to 136° C.

Synthesis of Compound (IV-17)

18.1 g (0.1 mol) of 2-methylthiobenzothiazole and 18 g (0.15 mol) of propane sultone were reacted in an oil bath at 130° C. without solvent for 1 hour. After the reaction, 50 ml of xylene was added to the reaction mixture and decanted. Then 50 ml of acetone was added and decanted. 50 ml of water and then an aqueous solution of 28.8 g (0.12 mol) of sodium sulfide were added and the mixture was stirred at room temperature. The crystals thus-deposited were collected by filtration and recrystallized from a 20% water-containing isopropyl alcohol to obtain 10 g (yield 32%) of the desired compound. Melting point of the compound was 312° C. (decomp.).

Other compounds represented by formula (IV) can be synthesized by reference to the above described synthesis examples, and the literature cited below. K. C. Kennard and J. A. Van Allen, *J. Org. Chem.*, Vol. 24, pages 470 to 473 (1959), R. W. Lamon and W. J. Humphlett, *J. Heterocycl. Chem.*, Vol. 4, pages 605 to 609 (1967), M. Ohara, Japanese Patent Publication No. 26203/64, and M. Morita, *Yakushi*, Vol. 82, pages 36 to 45 (1962).

The amount added of compound represented by formulae (II), (III), or (IV) is varied depending on a kind of the compound; generally a range of from $2 \times 10^{-5}$ mol/mol Ag to 20 mol/mol Ag is used, and preferably a range of from $10^{-4}$ mol/mol Ag to 2 mol/mol Ag is used. In more detail, with a compound of formula (II), a range of from $2 \times 10^{-5}$ mol/mol Ag to 2.5 mol/mol Ag, and preferably a range of from $10^{-4}$ mol/mol Ag to $3 \times 10^{-2}$ mol/mol Ag is used. With a compound of formula (III), a range of from $10^{-4}$ mol/mol Ag to 2 mol/mol Ag, and preferably from $5 \times 10^{-4}$ mol/mol Ag to $2 \times 10^{-1}$ mol/mol Ag is used. With a compound of formula (IV), a range of from $10^{-3}$ mol/mol Ag to 20 mol/mol Ag, and preferably from $5 \times 10^{-3}$ mol/mol Ag to 2 mol/mol Ag is used.

For the incorporation of a compound represented by formula (i) and a compound represented by formula (II), (III) or (IV) in the light-sensitive material, those methods usually used for the addition of additives to photographic emulsions can be employed. For example, when the compound is water-soluble, it is added as an aqueous solution in a suitable concentration to the photographic emulsion or light-insensitive hydrophilic collocidal solution. On the other hand, when the compound is insoluble or sparingly soluble in water, it is dissolved in a solvent which is selected from organic solvents compatible with water, such as alcohols, glycols, ketones, esters, amides and the like and which exert no adverse influences on the photographic characteristics, and it is added as a solution. In addition, those known methods usually used when water-insoluble (so-called oil-soluble) couplers are added to emulsions in a dispersion form can be employed.

The compound represented by formula (I) and compound represented by formula (II), (III), or (IV) may be added to different layers or may be added to the same layer. The photographic constituting layers of the light-sensitive material to which these compounds are added include conventionally employed layers, for example, a silver halide emulsion layer a subbing layer, an intermediate layer, an overcoating layer and the like. However, it is particularly preferred to add the compounds to a silver halide emulsion layer or a hydrophilic colloid layer adjacent thereto.

The silver halide particles as used in the present invention are of the surface latent image type. That is, they are not substantially of the internal latent image type. Specifically, the expression "surface latent image type" as used herein means that where, after from 1 to 1/100 second exposure the development of a photographic light-sensitive material which is prepared by coating on a transparent support conventionally used a silver halide emulsion that does not contain the compound represented by formula (I) used in the present invention, and developing is carried out by a surface development method (A) and an internal development method (B) as described below, the sensitivity obtained by the surface development method (A) is greater than that obtained by the internal development method (B). The sensitivity as herein is defined as follows:

$S = (100/Eh)$ wherein S is sensitivity, and Eh is an exposure amount required for obtaining a density $\frac{1}{2}(D_{max} + D_{min})$ which is just intermediate between the maximum density ($D_{max}$) and the minimum density ($D_{min}$).

Surface Development Method (A)

A light-sensitive material is developed at 20° C. for 10 minutes by use of a developer having the following formulation:
N-Methyl-p-aminophenol Hemisulfate: 2.5 g,
Ascorbic Acid: 10.0 g,
Sodium Metaborate Tetrahydrate: 35.0 g,
Potassium Bromide: 1.0 g,
Water to make: 1 liter.

Internal Development Method (B)

A light-sensitive materials is processed in a bleaching solution containing 3 g/l of potassium ferricyanide and 0.0125 g/l of phenosafranine at about 20° C. for 10 minutes, then washed with water for 10 minutes, and thereafter developed at 20° C. for 10 minutes in a developer having the following formulation:
N-Methyl-p-aminophenol Hemisulfate: 2.5 g,
Ascorbic Acid: 10.0 g,
Sodium Metaborate Tetrahydrate: 35.0 g,
Potassium Bromide: 1.0 g,
Sodium Thiosulfate: 3.0 g,
Water to make: 1 liter.

If the emulsion used in the present invention is not of the surface latent image type, not only a negative gradation, but also a positive gradation is formed, and the objects of the present invention cannot be attained.

Silver halide for use in the silver halide light-sensitive material of the present invention includes silver chloride, silver chlorobromide, silver bromide, silver iodobromide, and silver iodochlorobromide.

The average grain size of silver halide particles is preferably not more than $0.7\mu$ and more preferably not more than $0.4\mu$. The average grain size is a term which is ordinarily used by those in the art of silver halide photography and can easily be understood. By the grain size is meant a grain diameter where the grains are spherical or approximately spherical. Where the grains are cubic, it is calculated from the equation: (an edge length) $\times \sqrt{4/\pi}$. The average is an arithmetical or geometric mean calculated based on projected grain areas. The measurement of the average grain size can be effected by referring, for example, to C. E. K. Mees and T. H. James, *The Theory of The Photographic Process*, 3rd Ed., pp. 36–43, Macmillan Co., (1966).

As a binder or a protective colloid for the photographic emulsion of the light-sensitive material for use in this invention, it is advantageous to use gelatin. Of course, other hydrophilic colloids can be used, including gelatin derivatives, graft polymers of gelatin and other polymers; proteins such as albumin, casein, etc.;

cellulose derivatives such as hydroxyethyl cellulose, carboxymethyl cellulose, cellulose sulfate, etc.; various kinds of hydrophilic synthetic high molecular weight compounds, for example, homo- or copolymers such as polyvinyl alcohol, polyvinyl alcohol partial acetal, poly-N-vinyl pyrrolidone, polyacrylic acid, polymethacrylic acid, polyacrylamide, polyvinyl imidazole, polyvinyl pyrazole, etc.

In the photographic light-sensitive material, a chemical sensitizer for a silver halide emulsion, for example, gold, platinum, palladium, iridium, a thiosulfate, etc., a sensitizing dye, for example, a cyanine dye, a merocyanine dye, etc., an anti-irradiation dye, for example, an oxonol dye, a hemioxonol dye, a merocyanine dye, etc., a hardening agent, for example, a chromium salt, an aldehyde, an N-methylol compound, a dioxane derivative, an active vinyl compound (such as 1,3,5-triacryloyl-hexahydro-s-triazine, bis(vinylsulfonyl)methyl ether, etc.), an active halogen compound (such as 2,4-dichloro-6-hydroxy-s-triazine, etc.), etc., can be used. With respect to these compounds, there are described in greater detail in *Research Disclosure*, No. 17643 (December, 1978), and Japanese Patent Application (OPI) Nos. 1936/81 and 9743/81.

In the method of forming photographic images of the present invention, the above described silver halide photographic light-sensitive material after imagewise exposure is processed with an aqueous alkaline activator solution having a pH of 11.5 or more.

The imagewise exposure can be carried out in a conventional manner. Also, the imagewise exposure is conducted by the so-called "dot exposure" in which as in the exposure of conventional lith type light-sensitive material, the original image is exposed through a contact screen. In the method of the present invention, it is not necessary to specially select a contact screen which is suitable to the light-sensitive material to be used, which is different from the conventional substituents for lith type light-sensitive material as described in Japanese patent application (OPI) No. 22438/1976 and U.S. Pat. No. 2,419,975. Thus the present invention is advantageous in that by use of the same contact screen as used in the conventional lith type light-sensitive material, equal screen range can be obtained.

The light-sensitive material which has been imagewise exposed to light is processed by an activator aqueous solution of the present invention.

The aqueous alkaline activator solution used in the present invention may contain components which are used in conventional lith type developers except for the developing agents themselves. Components which can be incorporated in the activator aqueous solution include, in addition to alkali agents, such as alkali metal hydroxides (e.g., sodium hydroxide, potassium hydroxide), alkali metal carbonates (e.g., sodium carbonate, potassium carbonate, etc.), alkali metal phosphates (e.g., sodium primary phosphate, potassium tertiary phosphate, etc.), alkali metal borates (e.g., sodium borate, sodium metaborate, borax, etc.) and the like, pH buffers, bromides, iodides, antioxidants (e.g., sodium sulfite, potassium metabisulfite, etc.), and the like. Furthermore, if desired, the activator aqueous solution may contain organic solvents (e.g., diethylene glycol, triethylene glycol, diethanolamine, triethanolamine, etc.), water softeners (e.g., sodium tetrapolyphosphate, sodium hexametaphosphate, sodium nitrilotriacetate, ethylenediaminetetraacetic acid or its sodium salt, etc.), hardeners (e.g., glutaraldehyde, etc.), viscosity providing agents (e.g., carboxymethyl cellulose, hydroxyethyl cellulose, etc.), toning agents, surface active agents, deforming agents, and the like. The amounts of these additives to be used can be the same as in conventional aqueous activator solutions and these are well known to one skilled in the art.

The conditions under which the light-sensitive material is processed with the activator aqueous solution of the present invention can be determined properly. While the usual processing temperature is in the range of from 18° C. to 50° C., the processing of the present invention can be carried out at temperatures falling outside this range.

The processing using the activator aqueous solution of the present invention is usually carried out by immersing the light-sensitive material in the activator aqueous solution described above. During this immersion, the activator aqueous solution can be stirred. For this stirring there can be employed various known methods, for example, a method using stirring blades and a method of blowing inert gases thereinto. According to the method of the present invention, the variation of the dot quality can be prevented owing to the change in the state of stirring, such as a change in stirring means, a change in stirring speed, etc.

In the method of forming dot images according to the present invention, when the processing using the above described activator aqueous solution is carried out in the presence of polyalkylene oxide compounds or their derivatives as described in Japanese Patent Application (OPI) No. 37732/79, much better dot quality can be obtained.

The polyalkylene oxide compounds or derivatives thereof as used in the present invention have average molecular weights of at least 600, and they may be incorporated in the silver halide light-sensitive material or the alkaline activator aqueous solution.

Polyalkylene oxide compounds or derivatives thereof which can be used in the present invention include condensation products of polyalkylene oxides composed of at least 10 units of alkylene oxide containing 2 to 4 carbon atoms (e.g., ethylene oxide, propylene-1,2-oxide, butylene-1,2-oxide, etc., preferably ethylene oxide) and compounds containing at least one active hydrogen atom (e.g., water, aliphatic alcohols, aromatic alcohols, aliphatic acids, organic amines, hexytol derivatives, etc.), and block copolymers of two or more polyalkylene oxides.

Specific examples of such polyalkylene oxide compounds and derivatives thereof are as follows:
Polyalkylene glycols,
Polyalkylene glycol alkyl ethers,
Polyalkylene glycol aryl ethers,
Polyalkylene glycol alkylaryl ethers,
Polyalkylene glycol esters,
Polyalkylene glycol aliphatic acid amides,
Polyalkylene glycol amines,
Polyalkylene glycol block copolymers,
Polyalkylene glycol graft polymers.

Two or more polyalkylene oxide chains may be contained in the molecule. In this case, each polyalkylene oxide chain may be composed of less than 10 alkylene oxide units, but the total alkylene oxide units in the molecule should be at least 10. Where two or more polyalkylene oxide chains are contained in the molecule, they may be composed of different alkylene oxide units, for example, ethylene oxide and propylene oxide. Preferred polyalkylene oxide compounds or derivatives thereof as used in the present invention are those containing from 14 up to 100 of alkylene oxide units.

The polyalkylene oxide compound or derivative thereof is generally added to the silver halide light-sensitive material in an amount ranging from $5 \times 10^{-4}$ g to 5 g per mol of silver halide, and preferably from $1 \times 10^{-3}$ g to 1 g per mol of silver halide. On the other hand, where it is added to the activator aqueous solution, it is generally added in an amount of at least $1 \times 10^{-2}$ g per liter of the activator solution, and preferably in an amount ranging from $5 \times 10^{-2}$ g to 40 g per liter of the activator solution.

Following to the processing with the above-described activator aqueous solution, the light-sensitive material is subjected to fixing processing in a conventional manner.

As a fixing solution, fixing solutions having generally used compositions can be employed. As a fixing agent, an organic sulfur compound which is known to have the function of a fixing agent can be used, as well as a thiosulfate, a thiocyanate, etc. The fixing solution may contain a water-soluble aluminium salt as a hardening agent.

The processing temperature is usually selected in the range of from 18° C. to 50° C., but may be a temperature lower than 18° C. or a temperature higher than 50° C.

In addition to the activator processing and fixing processing described above, processing with other baths (for example, a stopping bath, a hardening bath, etc.) known in a black-and-white processing can be carried out. A period to which the processing with a subsidiary bath is applied and conditions of the processing can be decided in a conventional manner.

According to the method of forming photographic images of the present invention, the following effects which are obtained by processing a light-sensitive material containing a developing agent and the compound represented by the formula (I) with an activator can be attained. That is, the stability of the processing solution can markedly be increased and the control operation of the processing solution can be reduced in comparison with the conventional method wherein the lith type light-sensitive material and the infectious developer are used and furthermore a negative image of extremely high contrast which is equal in dot quality and screen range to that obtained by the conventional method can be obtained in a markedly short period of time. Additionally, in comparison with the method wherein the light-sensitive material to which the known hydrazine compound is added and the developer with a high pH value are used, the stabilities of not only the processing solution but also the light-sensitive material can be improved. Moreover, in comparison with the known method and the method wherein the light-sensitive material to which only hydroquinone is added and the activator to which a hydrazine compound is added are used, there can be obtained a negative image of very high contrast which is markedly excellent in dot quality and screen range. In addition, no special choice of contact screen is required, and by using a contact screen used in the exposure of the usual lith type light-sensitive material, practically the same screen range as in the lith type light-sensitive material can be obtained.

In addition to the above described effects, by incorporating the compound represented by the general formula (II), (III) or (IV) into the light-sensitive material, there can be obtained the great advantage that the dot quality is further improved and no variation in dot quality occurs even if the stirring conditions of the activator varies.

The present invention will be explained in greater detail with reference to the following examples, but the present invention is not limited thereto.

EXAMPLE

By adding an aqueous solution of silver nitrate and an aqueous solution of potassium bromide at the same time over a period of 50 minutes to an aqueous solution of gelatin kept at 50° C. while maintaining the pAg at 7.9, a silver bromide emulsion with an average grain size of $0.25\mu$ was produced. After the removal of soluble salts in a conventional manner, sodium thiosulfate was added to the emulsion in the amount of 43 mg per mole of silver bromide and then the silver bromide emulsion was subjected to chemical ripening at 60° C. for 60 minutes.

To the silver bromide emulsion were added hydroquinone dissolved in a 10% aqueous solution of gelatin, 5-methylbenzotriazole as an antifogging agent and 3-carbotymethyl-5-[(3-ethyl-2-thiazolidinylidene)ethylidene]rhodanine as a sensitizing dye. Then the resulting mixture was coated on a cellulose triacetate film so that the amount of silver was 40 mg per 100 cm² of the film. This film was designated as Film No. 1, the amount of the hydroquinone coated was 20 mg per 100 cm².

In the same manner as described in the preparation of Film No. 1, film samples were prepared except that a compound of group (I) which is within the scope of the general formula (I) and a compound of group (II) which is within the scope of formula (II), (III) or (IV) were added to an emulsion in the amount shown in Table 1 below, respectively. These films were designated as Film Nos. 2 to 43.

By use of a 150 line magenta contact screen these films were exposed to light through an exposure wedge for sensitometry and thereafter they were developed at 20° C. for 10 seconds with an alkaline activator having the composition as described below, wherein in one case the activator was stirred and in the other case it was not stirred, stopped, fixed, washed with water and dried to examine their photographic characteristics. The stirring of the activator was carried out by blowing therein a predetermined amount (100 ml/min.) of nitrogen during the development through fine openings provided on the side walls of a pipe which had been placed in a one liter activator bath at the bottom thereof.

| Composition of activator | |
|---|---|
| Sodium Sulfate | 15.0 g |
| Sodium Hydroxide | 44.0 G |
| Sodium Bromide | 7.0 g |
| Water to make | 1 liter |

The results of the dot quality thus obtained are shown in Table 1. In Table 1, the dot quality was visually evaluated in five grades, in which (1) indicates the best and (5), the worst. As a dot original plate for plate-making, only (1) and (2) are usable, and (3), (4) and (5) are unsatisfactory.

From the results as illustrated in Table 1, it can be seen that the dot quality is maintained constant irrespective of the stirring conditions of the processing, and furthermore it was improved.

TABLE 1

| Film No. | Compound of Group (I) | Amount Added (mol/mol Ag) | Compound of Group (II) | Amount Added (mol/mol Ag) | Dot Quality Activator With Stirring | Dot Quality Activator Without Stirring |
|---|---|---|---|---|---|---|
| 1 | not added | — | not added | — | 5 | 5 |
| 2 | I - 2 | $1.2 \times 10^{-3}$ | not added | — | 3 | 4 |
| 3 | I - 2 | $1.2 \times 10^{-3}$ | II - (1) | $2.5 \times 10^{-3}$ | 2 | 2 |
| 4 | I - 2 | $1.2 \times 10^{-3}$ | II - (2) | $1.5 \times 10^{-3}$ | 1 | 1 |
| 5 | I - 2 | $1.2 \times 10^{-3}$ | II - (12) | $1.5 \times 10^{-3}$ | 1 | 1 |
| 6 | I - 2 | $1.2 \times 10^{-3}$ | II - (17) | $1.5 \times 10^{-3}$ | 1 | 1 |
| 7 | I - 2 | $1.2 \times 10^{-3}$ | II - (22) | $1.0 \times 10^{-3}$ | 1 | 1 |
| 8 | I - 22 | $5.0 \times 10^{-5}$ | not added | — | 3 | 4 |
| 9 | I - 22 | $5.0 \times 10^{-5}$ | II - (1) | $1.5 \times 10^{-3}$ | 1 | 1 |
| 10 | I - 22 | $5.0 \times 10^{-5}$ | II - (2) | $1.5 \times 10^{-3}$ | 1 | 1 |
| 11 | I - 22 | $5.0 \times 10^{-5}$ | II - (12) | $1.5 \times 10^{-3}$ | 1 | 1 |
| 12 | I - 22 | $5.0 \times 10^{-5}$ | II - (17) | $1.5 \times 10^{-3}$ | 1 | 1 |
| 13 | I - 22 | $5.0 \times 10^{-5}$ | II - (22) | $1.0 \times 10^{-3}$ | 2 | 2 |
| 14 | I - 43 | $2.0 \times 10^{-5}$ | not added | — | 3 | 4 |
| 15 | I - 43 | $2.0 \times 10^{-5}$ | II - (1) | $2.5 \times 10^{-3}$ | 2 | 2 |
| 16 | I - 43 | $2.0 \times 10^{-5}$ | II - (2) | $1.5 \times 10^{-3}$ | 1 | 1 |
| 17 | I - 43 | $2.0 \times 10^{-5}$ | II - (12) | $1.5 \times 10^{-3}$ | 1 | 1 |
| 18 | I - 43 | $2.0 \times 10^{-5}$ | II - (17) | $1.5 \times 10^{-3}$ | 1 | 1 |
| 19 | I - 43 | $2.0 \times 10^{-5}$ | II - (22) | $1.0 \times 10^{-3}$ | 2 | 2 |
| 20 | I - 2 | $1.2 \times 10^{-3}$ | III - (1) | $2.0 \times 10^{-1}$ | 1 | 1 |
| 21 | I - 2 | $1.2 \times 10^{-3}$ | III - (2) | $1.0 \times 10^{-1}$ | 1 | 1 |
| 22 | I - 2 | $1.2 \times 10^{-3}$ | III - (5) | $1.0 \times 10^{-1}$ | 2 | 2 |
| 23 | I - 2 | $1.2 \times 10^{-3}$ | III - (10) | $5.0 \times 10^{-2}$ | 2 | 2 |
| 24 | I - 22 | $5.0 \times 10^{-5}$ | III - (1) | $2.0 \times 10^{-1}$ | 1 | 1 |
| 25 | I - 22 | $5.0 \times 10^{-5}$ | III - (2) | $1.0 \times 10^{-1}$ | 1 | 1 |
| 26 | I - 22 | $5.0 \times 10^{-5}$ | III - (5) | $1.0 \times 10^{-1}$ | 2 | 2 |
| 27 | I - 22 | $5.0 \times 10^{-5}$ | III - (10) | $5.0 \times 10^{-2}$ | 2 | 2 |
| 28 | I - 43 | $2.0 \times 10^{-5}$ | III - (1) | $2.0 \times 10^{-1}$ | 1 | 1 |
| 29 | I - 43 | $2.0 \times 10^{-5}$ | III - (2) | $1.0 \times 10^{-1}$ | 1 | 1 |
| 30 | I - 43 | $2.0 \times 10^{-5}$ | III - (5) | $1.0 \times 10^{-1}$ | 2 | 2 |
| 31 | I - 43 | $2.0 \times 10^{-5}$ | III - (10) | $5.0 \times 10^{-2}$ | 2 | 2 |
| 32 | I - 2 | $1.2 \times 10^{-3}$ | IV - (1) | $5.0 \times 10^{-3}$ | 2 | 2 |
| 33 | I - 2 | $1.2 \times 10^{-3}$ | IV - (4) | $1.0 \times 10^{-2}$ | 1 | 1 |
| 34 | I - 2 | $1.2 \times 10^{-3}$ | IV - (11) | $1.5 \times 10^{-2}$ | 1 | 1 |
| 35 | I - 2 | $1.2 \times 10^{-3}$ | IV - (18) | $2.0 \times 10^{-2}$ | 2 | 2 |
| 36 | I - 22 | $5.0 \times 10^{-5}$ | IV - (1) | $5.0 \times 10^{-3}$ | 2 | 2 |
| 37 | I - 22 | $5.0 \times 10^{-5}$ | IV - (4) | $1.0 \times 10^{-2}$ | 1 | 1 |
| 38 | I - 22 | $5.0 \times 10^{-5}$ | IV - (11) | $1.5 \times 10^{-2}$ | 1 | 1 |
| 39 | I - 22 | $5.0 \times 10^{-5}$ | IV - (18) | $2.0 \times 10^{-2}$ | 2 | 2 |
| 40 | I - 43 | $2.0 \times 10^{-5}$ | IV - (1) | $5.0 \times 10^{-3}$ | 2 | 2 |
| 41 | I - 43 | $2.0 \times 10^{-5}$ | IV - (4) | $1.0 \times 10^{-2}$ | 1 | 1 |
| 42 | I - 43 | $2.0 \times 10^{-5}$ | IV - (11) | $1.5 \times 10^{-2}$ | 1 | 1 |
| 43 | I - 43 | $2.0 \times 10^{-5}$ | IV - (18) | $2.0 \times 10^{-2}$ | 2 | 2 |

Further, the screen range of each sample was measured (using the difference between the logarithm of an exposure amount providing a dot area of 5% and that of an exposure amount providing a dot area of 95%). The screen range of the sample in which the compound represented by formula (I) was not contained was about 1.20. On the other hand, the screen range of the samples in which the compound represented by formula (I) was contained was about 1.40 and that of the samples in which the compound represented by formula (I) and the compound represented by formula (II), (III) or (IV) was also about 1.40. This value of screen range was almost equal to that obtained by the infectious development of a conventional lith film exposed using the same contact screen as was used.

Furthermore, the gamma ($\gamma$) value of Film No. 1 was lower than 10, but that of all other film samples was more than 10.

While the invention has been described in detail and with reference to specific embodiments thereof, it will be apparent to one skilled in the art that various changes and modifications can be made therein without departing from the spirit and scope thereof.

What is claimed is:

1. A method of forming a photographic image which comprises development processing, with an alkaline activator solution, an imagewise exposed silver halide photographic light-sensitive material comprising a support having thereon at least one surface latent image silver halide emulsion layer and at least one hydrophilic colloid layer, and containing in at least one layer selected from the group consisting of a silver halide emulsion layer and a hydrophilic colloid layer (1) a developing agent;
  (2) an acylhydrazine compound represented by formula (I):

$$R^1NHNHCOR^2 \qquad (I)$$

wherein $R^1$ represents an unsubstituted or substituted aryl group or alkyl group; and $R^2$ represents a hydrogen atom, or an unsubstituted or substituted aryl group or alkyl group; and (3) at least one compound represented by formula (II):

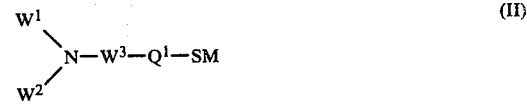

wherein each of $W^1$ and $W^2$ can represent a hydrogen atom or an aliphatic group or $W^1$ and $W^2$ are bonded to each other to form a ring; $W^3$ represents a divalent aliphatic group; $Q^1$ represents a simple bond or a divalent heterocyclic group containing a nitrogen atom, an oxygen atom, or a sulfur atom; and M represents a hydrogen atom, an alkali metal atom, an alkaline earth metal atom, a quarternary ammonium salt, a quartenary phosphonium salt, or an amidino group, or an inorganic acid salt or an organic acid salt thereof.

2. A method of forming a photographic image as in claim 1, wherein $R^1$ represents an unsubstituted or substituted phenyl group.

3. A method of forming a photographic image as in claim 1, wherein the amount of the compound represented by the general formula (I) is from $10^{-8}$ mol/mol Ag to $10^{-1}$ mol/mol Ag.

4. A method of forming a photographic image as in claim 1, wherein the developing agent is a dihydroxybenzene.

5. A method of forming a photographic image as in claim 1, wherein the developing agent is hydroquinone.

6. A method of forming a photographic image as in claim 1, wherein an amount of the developing agent is from 0.1 to 5 mol per mol of silver halide.

7. A method of forming a photographic image as in claim 1, wherein the aliphatic group represented by $W^1$ or $W^2$ is an unsubstituted or substituted alkyl group, alkenyl group, or alkynyl group, each of these groups containing from 1 to 12 carbon atoms and wherein the substituents are selected from a phenyl group, a substituted phenyl group, an alkoxy group, an alkylthio group, a hydroxy group, a carboxy group, a sulfo group, an alkylamino group, and an amino group.

8. A method of forming a photographic image as in claim 1, wherein the ring formed from $W^1$ and $W^2$ is a 5-membered or 6-membered saturated heterocyclic ring.

9. A method of forming a photographic image as in claim 1, wherein each of $W^1$ and $W^2$ represents an alkyl group containing from 1 to 3 carbon atoms.

10. The method of forming a photographic image as in claim 1, wherein the divalent group represented by $W^3$ is $-Q^3-$ or $-Q^3-S-$, wherein $Q^3$ represents a saturated or unsaturated aliphatic group containing from 1 to 6 carbon atoms and when $Q^1$ represents a simple bond, $W^3$ is $Q^3$.

11. A method of forming a photographic image as in claim 1, wherein the divalent heterocyclic group represented by Q, is a 5-membered or 6-membered aromatic heterocyclic group.

12. A method of forming a photographic image as in claim 1, wherein the amount of the compound represented by the formula (II) is from $2 \times 10^{-5}$ mol/mol Ag to 2.5 mol/mol Ag.

13. A method of forming a photographic image as in claim 1, wherein the compound represented by formula (I) and compound represented by formula (II), are present in a silver halide emulsion layer or a hydrophilic colloid layer adjacent thereto.

14. A method of forming a photographic image as in claim 1, wherein the compound represented by formula (I), compound represented by formula (II), and the developing agent are present in the silver halide emulsion layer.

15. A method of forming a photographic image as in claim 1, wherein the alkaline activator solution is an aqueous solution having a pH of at least 11.5.

16. A method of forming a photographic image as in claim 1, wherein the processing is carried out in the presence of polyalkylene oxide compound or a derivative thereof.

17. The method of forming a photographic image as in claim 1, wherein the polyalkylene oxide compound or a derivative thereof is present in the silver halide light-sensitive material or in the alkaline activator solution.

* * * * *